United States Patent [19]

Ketharanathan

[11] Patent Number: 4,466,139
[45] Date of Patent: Aug. 21, 1984

[54] VASCULAR PROSTHESES

[76] Inventor: Vettivetpillai Ketharanathan, 35 Degraves St., Parkville, Victoria, Australia

[21] Appl. No.: 305,634

[22] PCT Filed: Oct. 29, 1980

[86] PCT No.: PCT/AU80/00080
§ 371 Date: Sep. 21, 1981
§ 102(e) Date: Sep. 21, 1981

[87] PCT Pub. No.: WO82/00091
PCT Pub. Date: Jan. 21, 1982

[30] Foreign Application Priority Data
Jul. 1, 1980 [AU] Australia .............................. PE4308

[51] Int. Cl.³ .............................................. A61F 1/00
[52] U.S. Cl. ....................................................... 3/1.4
[58] Field of Search .................................. 3/1, 1.4, 1.5

[56] References Cited
U.S. PATENT DOCUMENTS
3,894,530 7/1975 Dardik et al. ................................ 3/1
3,974,526 8/1976 Dardik et al. ......................... 3/1.4 X
4,120,649 10/1978 Schechter ................................ 3/1.4

OTHER PUBLICATIONS
Hershey, F. and Calman, C., "Atlas of Vascular Surgery", 1973, C. Mosby Company, pp. 33-34.

Primary Examiner—Richard J. Apley
Assistant Examiner—David J. Isabella
Attorney, Agent, or Firm—Cushman, Darby & Cushman

[57] ABSTRACT

A vascular prosthesis is produced by subjecting a length of animal ureter to glutaraldehyde tanning. The lumen of the ureter is dilated and the ureter is set in the dilated configuration by the tanning process. The ureter may be strengthened by a surrounding sheath of polyester mesh.

Ureters for use in the invention can be obtained from a wide range of animal species, but preferably from cattle and sheep.

Prostheses can be produced in accordance with the invention for a wide range of revascularization surgery procedures in human patients.

11 Claims, 3 Drawing Figures

VASCULAR PROSTHESES

TECHNICAL FIELD

This invention relates to the field of surgery and more particularly to revascularization surgery.

As discussed in the specification of my copending Australian Pat. application No. 47208/79 (PD 4475) and corresponding U.S. Pat. application Ser. No. 041,620, now U.S. Pat. No. 4,319,363, the majority of deaths in the Western world are due to impaired arterial flow to distal tissues and revascularization surgery has become very common.

At the present time there are severe problems in obtaining suitable conduits for many revascularization procedures and it would be most desirable to have a bank of vascular prostheses, available in a range of diameters, which can give results comparable to autogenous saphenous vein grafts.

The aforesaid copending applications describe a vascular prosthesis comprised of a tube of collageous tissue which has been subjected to glutaraldehyde tanning and which is preferably reinforced with a tube of fibre mesh. Such a prosthesis can be obtained by implanting a rod or tube within a living host animal and allowing collageous tissue to form around the implant. The implant and surrounding collageous tissue is subsequently removed and the collageous tissue then subjected to glutaraldehyde tanning.

I have now determined that animal ureters have adequate collagen content and luminal surface characteristics when subjected to glutaraldehyde tanning to perform satisfactorily as vascular grafts. This enables the preparation of vascular prostheses without the need for surgical procedures in host animals and it has been found that the resulting grafts can perform satisfactorily in wide ranging vascular situations. The ureters can be obtain from a wide range of animal species including humans, oxen, cows, sheep, goats, pigs, donkeys, camels, deer and kangaroos.

DISCLOSURE OF INVENTION

According to the invention there is provided a vascular prosthesis comprising a length of animal ureter which has been subjected to glutaraldehyde tanning. The invention also extends to the use of such a vascular prosthesis as a surgical graft in a living human patient.

The invention also provides a method of producing a vascular prosthesis for use as a surgical graft comprising subjecting a length of animal ureter to glutaraldehyde tanning.

Preferably, the ureter is encompassed by a fibre mesh sheath. Such sheath may, for example, be formed of a mesh woven from strands of multiple fine polyester fibres.

Preferably further, the wall of the lumen of the ureter is set in a dilated condition by the glutaraldehyde tanning so as to have a smooth, generally cylindrical surface.

BRIEF DESCRIPTION OF DRAWINGS

In the following detailed description of the preparation of vascular prostheses in accordance with the invention, reference will be made to the accompanying drawings in which.

BEST MODES OF CARRYING OUT THE INVENTION

In a typical preparation of vascular prostheses in accordance with the invention, ureters from human cadavers, oxen or other animals are obtained under abattoir conditions. They are transported to an aseptic area where they are cleaned of fat and adherent tissue. Glass rods of 2 mm to 10 mm diameter, depending on the size of the ureters, are inserted into the lumen of the ureters so that the ureters are supported on and stretched by the rods. More specifically, the rods are of such size as to dilate the lumen of the ureters so that thin walls become compressed into a close packed structure with a smooth generally cylindrical surface. This will be described more fully below with reference to FIGS. 1 and 2.

The lengths of the stretched ureters may vary from 10 cm to 60 cm according to the species of animal from which they are obtained. The glass rods and ureters are then covered with fine polyester mesh. This may be achieved by placing a tube of woven polyester mesh within a confining glass tube, then inserting the lumen on the glass rod through the mesh tube within the outer glass tube, and finally withdrawing the glass rod, the ureter and the enveloping mesh together as a unit from the outer glass tube.

The polyester mesh covered ureters containing the glass rods of predetermined diameter and length are subjected to glutaraldehyde tanning by immersion in buffered glutaraldehyde. The buffered glutaraldehyde may have a glutaraldehyde strength in the range 0.05% to 10% and preferably about 2.5%. The buffer may be a phosphate such as $Na_2HPO_4$ or $KH_2PO_4$ or a carbonate buffer. The pH of the bath may be in the range 2 to 8 and is preferably about 7.4.

The ureter may be immersed in the buffered glutaraldehyde at room temperature for between 4 hours and 100 hours, preferably for about 72 hours.

After glutaraldehyde tanning the mesh covered ureter is bleached by immersion in a bath of hydrogen peroxide to remove all free glutaraldehyde. The bleaching bath may contain hydrogen peroxide in the range 1% to 10% and preferably about 5%.

After bleaching the ureter may be dialysed in sterile water. More particularly, it may be successively immersed in three separate water baths and kept stirred in each bath for about 3 hours.

After glutaraldehyde tanning, bleaching and dialysing, the ureteric grafts are individually packed in glass cylinders in 50% alcohol for preservation and storage.

When a ureteric graft produced in the above manner is to be prepared for implantation, it is removed from its individual glass storage cylinder and slid off the supporting glass rod. It is then soaked in three separate baths of heparinised saline (10,000 units per litre). Preferably, it is held in each bath for about 20 minutes. It is then ready for surgical grafting.

Figure 1:
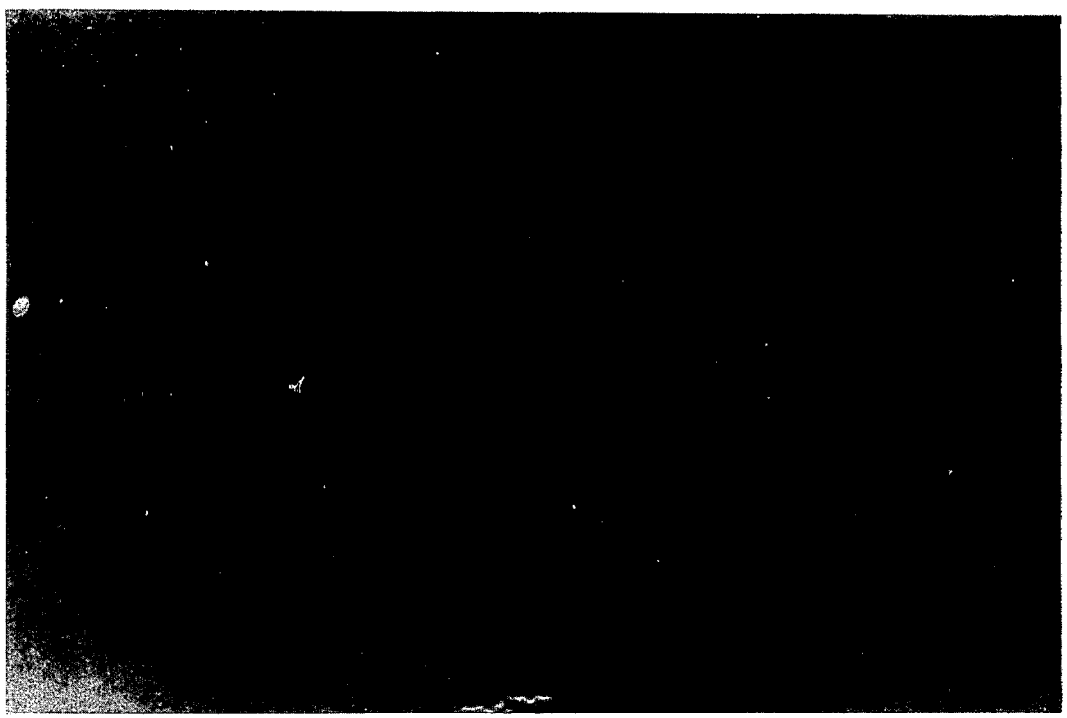
FIG. 1 is a reproduction of a photomicrograph showing a section through an ox ureter in its natural state.

In the accompanying drawings FIG. 1 shows a section through an ox ureter in its natural state. It can be seen that the wall, although circular, is loosely packed and the central lumen is very constricted and of stellate formation. The darker areas in the ureter wall show the collagen content.

Figure 2:
FIG. 2 is a reproduction of a photomicrograph showing a section through a vascular prosthesis produced in accordance with the invention.

FIG. 2 shows a section through a vascular prosthesis produced from an ox ureter in accordance with the invention. It can be seen that the lumen has been greatly dilated and the wall has been compressed to a compact structure having a smooth generally cylindrical surface, this structure being set by the glutaraldehyde tanning process. The bundles of dark spots appearing at the outside of the ureter are the strands of multiple fibres of the surrounding mesh sheath.

Figure 3:
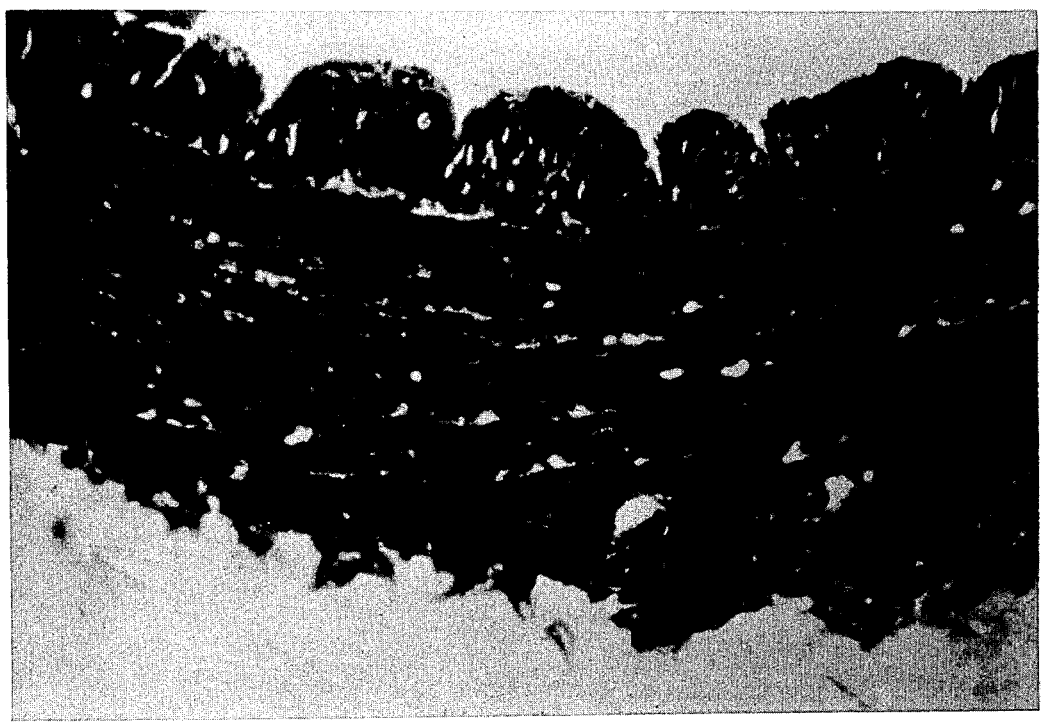
FIG. 3 is a reproduction of a photomicrograph showing a section through a human saphenous vein.

FIG. 3 shows a section through a human saphenous vein. This exhibits a bumpy surface of bulges and crevices and a collagen density less than that in the prosthesis of FIG. 2. The structure of prosthesis in FIG. 2 is superior to that of the human saphenous vein which is being widely used in revascularization surgery with success.

Tanned ureteric vascular grafts prepared in the above manner have been evaluated in the following experimental procedures:

I. ARTERIAL GRAFTS IN DOGS

Twelve adult mongrel dogs weighing 15 to 20 kg were anaesthetised and a mid-line laparotomy performed.

The first dog had a single bovine ureteric graft 10 cm long and 6 mm wide anastomised to the infrarenal aorta proximally and to the right common iliac artery distally. The terminal aorta was ligated. The graft remained patent for 17 months documented by arteriograms and inspection on sacrifice. Histological examination did not show any biodegradation or luminal narrowing.

The subsequent 11 dogs had a bovine ureteric graft and an ovine biosynthetic graft of 10 cm long and 6 mm wide (in accordance with my aforesaid copending applications) inserted as parallel vascular grafts. Their proximal anastomoses were to infrarenal aorta. The distal anastomoses were to the right and left common iliac arteries. The terminal aorta was ligated. All animals had patent grafts up to two years as documented by periodic angiograms.

II. SHUNTS IN PIGS

Nine anaesthetised four weeks old piglets weighing 7 to 10 kg were used to construct aortopulmonary shunts at left thoracotomy. The shunts were ovine ureteric grafts 6 mm wide and 3 cm long. Patency of the shunts of ureteric grafts were documented by haemodynamic measurements. All shunts were patent at four weeks. Similar shunts in piglets of same age and similar weight constructed with goretex and ovine biosynthetic grafts failed to maintain a shunt at four weeks.

III. VENOUS SEGMENTAL REPLACEMENTS IN RABBITS

In ten anaesthetised adult rabbits a mid-line laparotomy was performed. After cross-clamping, a segment of infrarenal inferior venacava was excised and was replaced by 3 cm long and 3 mm wide ureteric grafts produced from pig ureters. All rabbits survived this procedure. None of them have shown any evidence of inferior venacaval obstruction. The first two rabbits were explored at one and two weeks post-operatively and showed widely patent grafts.

IV. REVASCULARIZATION IN HUMAN PATIENTS

Four human patients have had limbs salvaged by lower limb revascularization using tanned bovine ureteric grafts produced in accordance with the invention. These patients still have viable limbs after periods ranging from three to six months from revascularization.

One patient has had two tanned bovine ureteric grafts implanted for myocardial revascularization with success. In both instances no conduit of apropriate size would have been available but for the present invention.

INDUSTRIAL APPLICABILITY

The above described results have established that animal ureters have adequate collageous content and luminal surface characteristics when subjected to glutaraldehyde processing in accordance with the invention and they can perform satisfactorily as vascular grafts. The experiment evaluation carried out for more than 2 years in 3 different species and in differing vascular situations has proved successful. The three differing situations of arterial, aorto-pulmonary shunts and segmental venous replacements imposed different types of stress on the ureteric grafts. In all cases the ureteric grafts performed successfully and consistently and their ability to remain patent in 3 mm diameters in a venous environment and their flexibility make them suitable for coronary grafts.

It has been found that bovine and ovine collagen have particularly desirable properties when subjected to glutaraldehyde tanning in accordance with the present invention. The reasons for this are not fully understood but grafts produced from cattle and sheep ureters have been most successful. It is therefore anticipated that long grafts for limb salvage would normally be produced from ox ureters whereas smaller grafts would be produced from ureters taken from calves or sheep.

1. A vascular prosthesis suitable for use as a surgical graft, comprising a length of animal ureter which has been structurally modified and set to provide a smooth luminal surface and has been subjected to glutaraldehyde tanning.

2. A vascular prosthesis as claimed in claim 1, wherein said length of animal ureter is supported by an external fibre mesh sheath.

3. A vascular prosthesis as claimed in claim 2, wherein said mesh is woven from strands of multiple fine polyester fibres.

4. A vascular prosthesis as claimed in claim 1, wherein the wall of the lumen of said ureter is set in a dilated condition by the glutaraldehyde tanning so as to have a smooth, generally cylindrical surface.

5. A vascular prosthesis suitable for use as a surgical graft, comprising a length of ovine ureter which has been structurally modified and set to provide a smooth luminal surface and been subjected to glutaraldehyde tanning with the lumen dilated such that the wall of the lumen is set by the tanning to exhibit a smooth, generally cylindrical lumen surface, the prosthesis further comprising a mesh sheath of woven synthetic fibres encompassing the tanned length of ureter.

6. A vascular prosthesis suitable for use as a surgical graft, comprising a length of bovine ureter which has been structurally modified and set to provide a smooth luminal surface and been subjected to glutaraldehyde tanning with the lumen dilated such that the wall of the lumen is set by the tanning to exhibit a smooth, generally cylindrical lumen surface, the prosthesis further comprising a mesh sheath of woven synthetic fibres encompassing the tanned length of ureter.

7. A method of producing a vascular prosthesis for use as a surgical graft comprising subjecting a length of animal ureter to glutaraldehyde tanning thereby structurally modifying and setting the ureter to provide a smooth luminal surface.

8. A method as claimed in claim 7, wherein a rod or tube is inserted into the lumen of the animal ureter prior to glutaraldehyde tanning whereby dilate the lumen wall such that it has a smooth generally cylindrically curved surface, the wall of the lumen is set in the dilated condition by the glutaraldehyde tanning, and the rod or tube is subsequently removed from the lumen.

9. A method as claimed in claim 8, wherein a fibre mesh is applied about the length of animal ureter while it is supported on the rod or tube to form an external supporting sheath for the prosthesis.

10. A method of producing a vascular prosthesis for use as a surgical graft, comprising the steps of:
   (1) inserting a rod or tube into the lumen of a length of ovine ureter whereby to dilate the lumen such that it has a smooth generally cylindrically curved surface,
   (2) applying a fibre mesh around the ureter while it is supported on the rod or tube to form an external supporting sheath,
   (3) subjecting the ureter to glutaraldehyde tanning while it is supported on the rod or tube whereby to structurally modify and set it in the dilated condition and provide a smooth luminal surface, and
   (4) removing the rod or tube from the lumen after tanning.

11. A method of producing a vascular prosthesis for use as a surgical graft, comprising the steps of:
   (1) inserting a rod or tube into the lumen of a length of bovine ureter whereby to dilate the lumen such that it has a smooth generally cylindrically curved surface,
   (2) applying a fibre mesh around the ureter while it is supported on the rod or tube to form an external supporting sheath,
   (3) subjecting the ureter to glutaraldehyde tanning while it is supported on the rod or tube whereby to structurally modify and set it in the dilated condition and provide a smooth luminal surface, and
   (4) removing the rod or tube from the lumen after tanning.

* * * * *